US00PP30949P2

(12) United States Plant Patent
van Duijnhoven

(10) Patent No.: US PP30,949 P2
(45) Date of Patent: Oct. 15, 2019

(54) ***ASPLENIUM* PLANT NAMED 'CAMPIO'**

(50) Latin Name: *Asplenium nidus*
Varietal Denomination: Campio

(71) Applicant: Vitro Plus, B.V., Burgh-Haamstede (NL)

(72) Inventor: Henk van Duijnhoven, Mariahout (NL)

(73) Assignee: Vitro Plus, B.V., Burgh-Haamstede (NL)

( * ) Notice: Subject to any disclaimer, the term of this patent is extended or adjusted under 35 U.S.C. 154(b) by 0 days.

(21) Appl. No.: 15/731,323

(22) Filed: May 25, 2017

(51) Int. Cl.
*A01H 5/00* (2018.01)

(52) U.S. Cl.
USPC ..... Plt./379
CPC ..... *A01H 5/00* (2013.01)

(58) Field of Classification Search
USPC ..... Plt./379
CPC ..... A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Asplenium nidus* cultivar named 'Campio' which is characterized by an upright growth habit, dark green foliage, broad leaves and irregularly incised margins with little undulation, and the stability of these characteristics from generation to generation.

2 Drawing Sheets

Latin name of the genus and species: The Latin name of the genus and species of the novel variety disclosed herein is *Asplenium nidus*.

Variety denomination: The inventive variety of *Asplenium nidus* disclosed herein has been given the variety denomination 'Campio'.

CROSS REFERENCE TO RELATED APPLICATIONS

This application claims priority to the Community Plant Variety Rights application number 2017/1157, filed Apr. 26, 2017, which is herein incorporated by reference.

BACKGROUND OF THE INVENTION

Parentage: 'Campio' originated as a naturally occurring, whole-plant mutation of *Asplenium nidus* 'FIMBRIATUM' (not patented). In June of 2013 the inventor discovered the mutation at his commercial greenhouse in Mariahout, The Netherlands, growing amongst a crop of *Asplenium nidus* 'FIMBRIATUM'. The mutation was noted for its unique foliage habit and was isolated for further observation in order to confirm the distinctness and stability of the characteristics first observed. After further evaluation it was determined that the unique characteristics of the candidate plant would prove favorable for commercial marketability. The new variety was given the breeder denomination 'Campio'.

Asexual Reproduction: Asexual reproduction of the new cultivar 'Campio', by way of mericloning, was first initiated in November of 2013 at a commercial laboratory in Burgh-Haamstede, The Netherlands. Through subsequent generations, the unique features of this cultivar have proven to be stable and true to type.

SUMMARY OF THE INVENTION

The cultivar 'Campio' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Campio'. These characteristics in combination distinguish 'Campio' as a new and distinct *Asplenium nidus* cultivar:

1. *Asplenium* 'Campio' exhibits an upright growth habit with leaves growing from a basal rosette forming a broad, inverted triangular-shaped plant form; and
2. *Asplenium* 'Campio' exhibits broad, dark green leaves; and
3. *Asplenium* 'Campio' exhibits irregularly incised leaf margins with very little undulation. .

BOTANICAL DESCRIPTION OF THE PLANT

Figure 1:
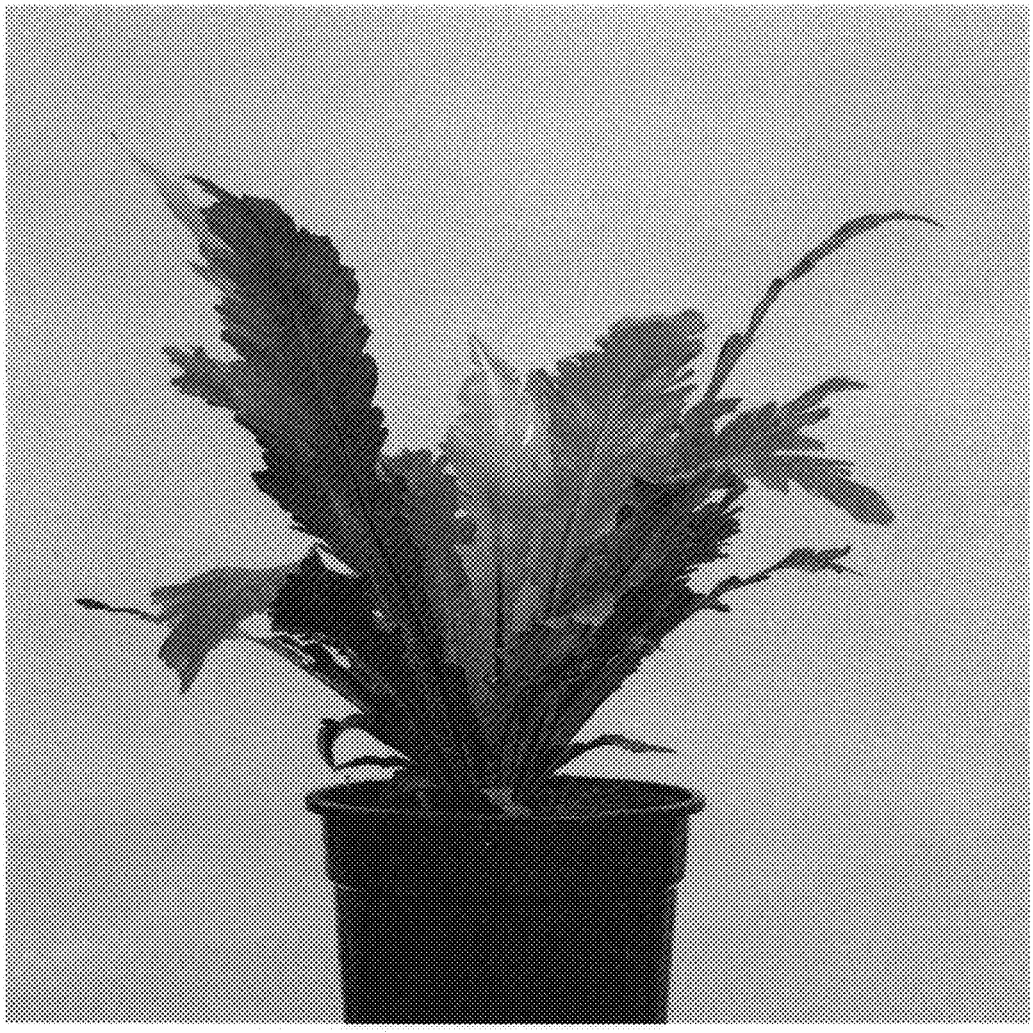
FIG. 1 illustrates, as nearly true as it is reasonably possible to make the same in color photographs of this type, an exemplary plant of 'Campio' grown in a commercial greenhouse in Mariahout, The Netherlands. This plant is approximately 8 month old, shown planted in a 17 cm container.
Figure 2:
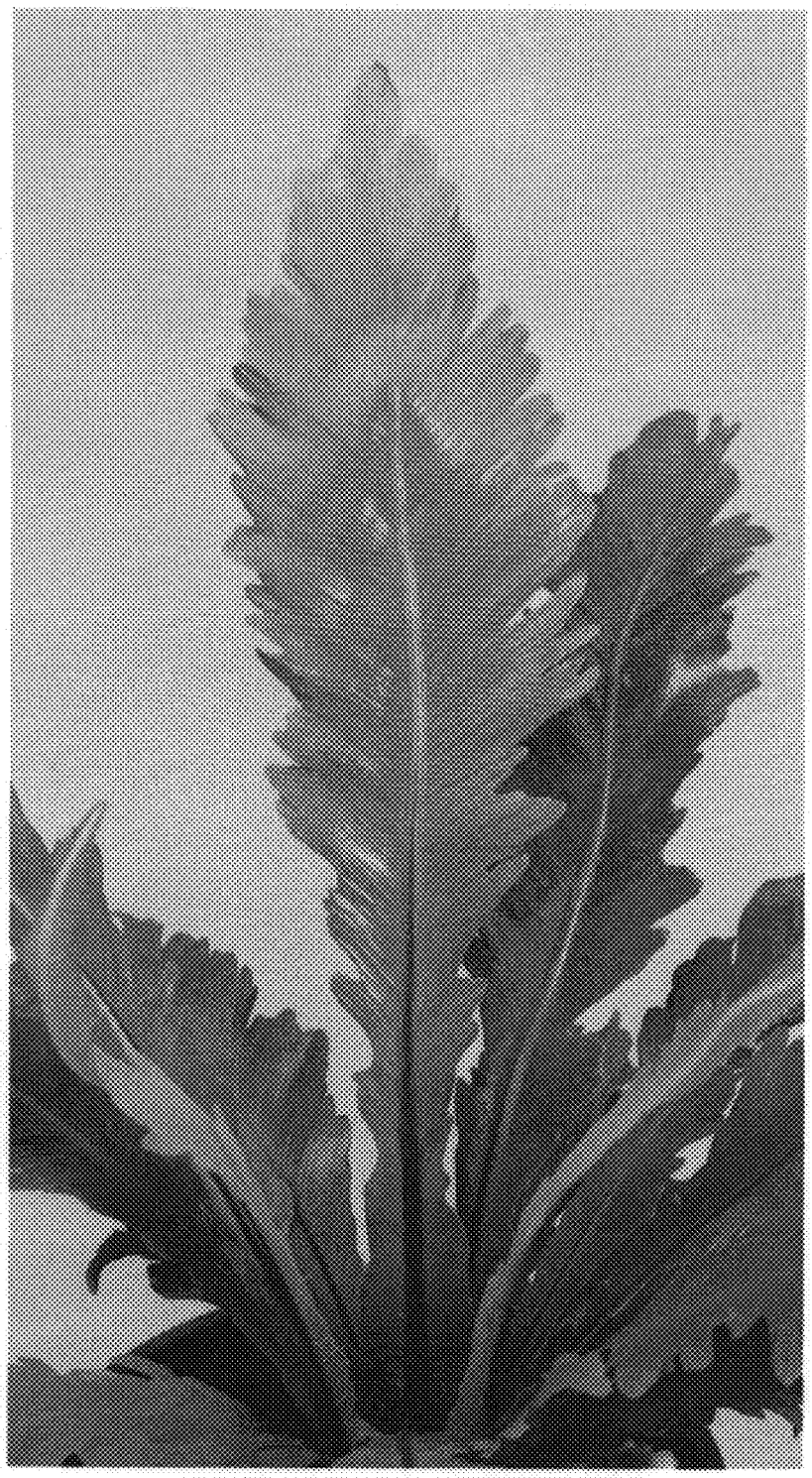
FIG. 2 illustrates, as nearly true as it is reasonably possible to make the same in color photographs of this type, the typical apical foliage habit of 'Campio'.

The following observations and measurements made in April of 2017 describe averages from a sample set of six specimens of 8 month old 'Campio' plants grown in 17 cm nursery containers at a greenhouse in Mariahout, The Netherlands. Plants were produced using conventional greenhouse production protocols which consisted of overhead irrigation, liquid fertilizer applications, and chemical pest control measures for aphids as required. Temperatures ranged from approximately 5 to 15 degrees Celsius during the day and 1 to 12 degrees Celsius at night. No photoperiodic treatments or artificial light was given to the plants.

Those skilled in the art will appreciate that certain characteristics will vary with older or, conversely, with younger plants. 'Campio' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'Campio' and a comparison with the parent, *Asplenium nidus* 'FIMBRIATUM', and closest known comparator are provided below.

Plant description:

*Growth habit*.—Herbaceous perennial fern with an upright growth habit; leaves growing from a basal rosette forming a broad, inverted triangular-shaped plant form.

*Height from soil level to top of foliar plane*.—29.5 cm, on average.

*Plant spread*.—Average of 44.5 cm.

*Growth rate*.—Moderate.

*Plant vigor*.—Moderate.

*Propagation*.—Type — Mericloning. Time to initiate roots — Approximately 80 days at about 25 degrees Celsius. Crop time — Approximately 26 weeks from propagation to a marketable plant.

*Disease and pest resistance or susceptibility*.—Neither susceptibility nor resistance to pests and diseases common to *Asplenium nidus* varieties.

*Environmental tolerances*.—Adapt to, at least, USDA Zones 10 to 13 and temperatures as high as 35 degrees Celsius; high tolerance to rain; moderate tolerance to wind.

Root system:

*General*.—Fine, well-branched fibrous roots.

*Color*.—Brown, nearest to 200B.

Foliage:

*Arrangement*.—Alternate; growing in basal rosettes.

*Division*.—Simple.

*Quantity*.—Approximately 22 leaves per plant.

*Dimensions*.—31.1 cm long and 8.2 cm wide, on average.

*Shape*.—Oblanceolate.

*Aspect*.—Flat.

*Attitude*.—Approximately 40 degrees to vertical.

*Apex*.—Narrow obtuse to bluntly acute.

*Base*.—Attenuate.

*Margin*.—Irregularly incised and occasionally deeply incised, giving the appearance of a lobed leaf margin; leaves are very slightly undulate.

*Pubescence, texture and luster of adaxial surface*.—Glabrous, smooth, and very glossy.

*Pubescence, texture and luster of abaxial surface*.—Glabrous, smooth, and very glossy.

*Color*.—Juvenile foliage, adaxial surface — Yellow-green, nearest to RHS 144A. Juvenile foliage, abaxial surface — Yellow-green, nearest to in between RHS 144A and 144B. Mature foliage, adaxial surface — Nearest to in between green, RHS 137A, and yellow-green, RHS 146A. Mature foliage, abaxial surface — Nearest to in between green, RHS 137A, and yellow-green, RHS 146A.

*Venation*.—Pinnate.

*Venation color, adaxial surface*.—The main vein is green, nearest to RHS NN137A, and is heavily suffused with brown towards the proximal end, nearest to in between RHS 200A and 200B. Secondary veins are in between green, RHS 137A, and yellow-green, RHS 146A.

*Venation color, abaxial surface*.—The main vein is green, nearest to RHS NN137A, and is heavily suffused with brown towards the proximal end, nearest to in between RHS 200A and 200B. Secondary veins are in between green, RHS 137A, and yellow-green, RHS 146A.

*Petiole*.—No petioles present, leaves sessile.

Sori: No sori present.

Comparisons With the Parent Plant

Plants of the new cultivar 'Campio' differ from the parent, *Asplenium nidus* 'FIMBRIATUM', in the following characteristics:

1. 'Campio' exhibits foliage which is much broader than that of the 'FIMBRIATUM'.
2. 'Campio' exhibits an irregularly incised leaf margin, whereas the leaf margins of 'FIMBRIATUM' are deeply serrated.

Comparisons With the Most Similar Variety

Plants of the new cultivar 'Campio' differ from the closest known comparator, *Asplenium nidus* 'Avis', in the following characteristics:

1. 'Campio' exhibits a more upright growth habit than that of 'Avis'.
2. 'Campio' exhibits foliage which is much broader than that of the 'Avis'.
3. 'Campio' exhibits foliage which is darker green than that of the 'Avis'.
4. 'Campio' exhibits less visible foliage venation than that of the 'Avis'.
5. 'Campio' exhibits an irregularly incised leaf margin, whereas the leaf margins of 'Avis' are entire to slightly incised.
6. The leaf margins of 'Campio' are very slightly undulated, whereas the leaf margins of 'Avis' are moderately to heavily undulated.

That which is claimed is:

1. A new and distinct variety of *Asplenium nidus* plant named 'Campio', substantially as described and illustrated herein.

* * * * *